United States Patent [19]
Cavalla et al.

[11] Patent Number: 6,166,041
[45] Date of Patent: Dec. 26, 2000

[54] 2-HETEROARYL AND 2-HETEROCYCLIC BENZOXAZOLES AS PDE IV INHIBITORS FOR THE TREATMENT OF ASTHMA

[75] Inventors: David J. Cavalla, Cambridge, United Kingdom; Mark Chasin, Manalapan, N.J.; John W F Whitehead, Hertfordshire, United Kingdom; Lesley Walton, Leicestershire, United Kingdom; Andrew C. Mansfield, Cambridge, United Kingdom

[73] Assignee: Euro-Celtique, S.A., Luxembourg

[21] Appl. No.: 08/963,054

[22] Filed: Nov. 3, 1997

Related U.S. Application Data

[63] Continuation-in-part of application No. 08/833,897, Apr. 10, 1997, abandoned, which is a continuation of application No. PCT/US95/14399, Oct. 11, 1995.

[51] Int. Cl.[7] .......................... A61K 31/44; A61K 31/47; A61K 31/505; A61K 31/495; C07D 413/00; C07D 215/18; C07D 215/00; C07D 217/00

[52] U.S. Cl. .......................... 514/338; 514/249; 514/253; 514/254; 514/256; 514/261; 514/262; 514/269; 514/274; 514/307; 514/309; 514/312; 514/314; 514/333; 544/264; 544/265; 544/276; 544/277; 544/315; 544/316; 544/319; 544/320; 544/333; 544/353; 544/354; 544/356; 544/364; 544/384; 544/398; 544/403; 546/141; 546/144; 546/148; 546/152; 546/153; 546/157; 546/158; 546/164; 546/165; 546/166; 546/167; 546/178; 546/179; 546/180; 546/256; 546/271.7

[58] Field of Search .................. 546/271.7, 141, 546/144, 148, 152, 153, 157, 158, 164, 165, 166, 167, 178, 179, 180, 256; 514/338, 249, 253, 254, 256, 261, 262, 269, 274, 307, 309, 312, 314, 333; 544/264, 265, 276, 277, 315, 316, 319, 320, 333, 353, 354, 356, 364, 384, 398, 403

[56] References Cited

U.S. PATENT DOCUMENTS

| | | | |
|---|---|---|---|
| Re. 31,429 | 10/1983 | Tull et al. | 544/277 |
| 2,320,654 | 6/1943 | Riester | 95/7 |
| 2,691,654 | 10/1954 | Hitchings | 260/247.5 |
| 2,844,577 | 7/1958 | Acker | 260/254 |
| 2,903,455 | 9/1959 | Strong et al. | 260/252 |
| 2,956,998 | 10/1960 | Baizer | 260/252 |
| 2,957,875 | 10/1960 | Lyttle et al. | 260/252 |
| 2,966,488 | 12/1960 | Shive et al. | 260/252 |
| 3,079,378 | 2/1963 | Schroeder | 260/211.5 |
| 3,129,225 | 4/1964 | Shapiro | 250/247.2 |
| 3,135,753 | 6/1964 | Hitchings | 540/265 |
| 3,136,771 | 6/1964 | Liechti et al. | 260/296 |
| 3,215,696 | 11/1965 | Denayer | 260/252 |
| 3,225,046 | 12/1965 | Zwahlen | 260/252 |
| 3,262,929 | 7/1966 | Okubu et al. | 260/240 |
| 3,470,164 | 9/1969 | Takamatsu | 260/240 |
| 3,491,091 | 1/1970 | Berger | 260/240 |
| 3,491,106 | 1/1970 | Freyermuth | 260/304 |

(List continued on next page.)

FOREIGN PATENT DOCUMENTS

| | | |
|---|---|---|
| 994351 | 8/1976 | Canada . |
| 0018136 | 10/1980 | European Pat. Off. . |
| 0178413 A1 | 4/1986 | European Pat. Off. . |

(List continued on next page.)

OTHER PUBLICATIONS

Cariuk et a. Chem. Abstr vol. 128 entry 153640, 1998.
"The Synthesis of Some 6 Thioxanthines", K.R.H. Wooldrige and R. Slack, J. Chem. Soc. 1962, Annex IV;1863–1868.

(List continued on next page.)

*Primary Examiner*—Mukund J. Shah
*Assistant Examiner*—Brenda Coleman
*Attorney, Agent, or Firm*—Davidson, Davidson & Kappel, LLC

[57] ABSTRACT

Novel compounds which are effective PDE IV inhibitors are disclosed. The present invention is directed to compounds having the general formula I

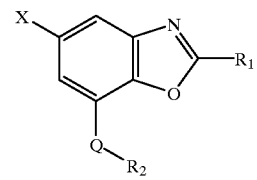

wherein:
  X is a halogen;
  Q is $-CH_2-CH_2-$, $-CH_2-$, a single or a double bond, or $-NR_1-$;
  $R_1$ is a $C_{3-7}$ monocyclic ring structure containing at least one carbon atom and comprising one or more chalcogen atoms selected from the group consisting of nitrogen, sulfur and oxygen, wherein the monocyclic ring is unsaturated, partially unsaturated or saturated, and is optionally substituted with alkyl, cycloalkyl, alkoxy, cycloalkoxy, hydroxy or halogen; or is a bicyclic structure, comprised of a phenyl ring fused to a monocyclic ring structure as defined above, or comprised of two fused monocyclic ring structures, each ring containing at least one carbon atom and comprising one or more chalcogen atoms selected from the group consisting of nitrogen, sulfur and oxygen, wherein the monocyclic ring is unsaturated, partially unsaturated or saturated, and is optionally substituted with alkyl, cycloalkyl, alkoxy, cycloalkoxy, hydroxy or halogen.
  $R_2$ is a phenyl group or a $C_{3-7}$ monocyclic ring structure containing at least one carbon atom and comprising one or more chalcogen atoms selected from the group consisting of nitrogen, sulfur and oxygen, wherein the monocyclic ring may be unsaturated, partially unsaturated or saturated, and is optionally substituted with alkyl, cycloalkyl, alkoxy, cycloalkoxy, hydroxy or halogen.

11 Claims, No Drawings

6,166,041
Page 2

U.S. PATENT DOCUMENTS

| | | | |
|---|---|---|---|
| 3,494,919 | 2/1970 | Collins et al. | 260/240 |
| 3,516,997 | 6/1970 | Takano et al. | 260/243 |
| 3,541,100 | 11/1970 | Ramirez et al. | 260/286 |
| 3,551,554 | 12/1970 | Herschler | 424/7 |
| 3,574,218 | 4/1971 | Hideg et al. | 260/293.4 |
| 3,586,670 | 6/1971 | Brenneisen | 260/240 |
| 3,590,029 | 6/1971 | Koch et al. | 260/211.5 |
| 3,626,018 | 12/1971 | Taylor | 260/670 |
| 3,636,039 | 1/1972 | Gruenman et al. | 260/309.7 |
| 3,647,812 | 3/1972 | Smith | 260/304 |
| 3,658,799 | 4/1972 | Eardley et al. | 260/243 C |
| 3,666,769 | 5/1972 | Jones | 260/304 |
| 3,669,979 | 6/1972 | Freyermuth | 260/304 |
| 3,674,781 | 7/1972 | Schinzel et al. | 260/240 |
| 3,681,328 | 8/1972 | Kurita et al. | 260/243 C |
| 3,686,238 | 8/1972 | Zaffaroni | 260/399 |
| 3,706,834 | 12/1972 | Schellenbaum et al. | 424/272 |
| 3,923,833 | 12/1975 | Gruenmann et al. | 260/340.5 |
| 3,962,452 | 6/1976 | Evans et al. | 424/272 |
| 4,020,165 | 4/1977 | Hubbard et al. | 424/270 |
| 4,025,636 | 5/1977 | Dunwell et al. | 424/269 |
| 4,025,637 | 5/1977 | Dunwell | 424/272 |
| 4,107,306 | 8/1978 | Voorhees | 424/248.51 |
| 4,146,721 | 3/1979 | Rainer | 548/374 |
| 4,167,628 | 9/1979 | Kormany | 542/454 |
| 4,233,303 | 11/1980 | Bergstrand et al. | 424/253 |
| 4,241,063 | 12/1980 | Naito et al. | 424/253 |
| 4,241,168 | 12/1980 | Arai et al. | 430/503 |
| 4,308,278 | 12/1981 | Schneider et al. | 424/273 |
| 4,361,699 | 11/1982 | Rasmusson et al. | 544/277 |
| 4,407,802 | 10/1983 | Graham et al. | 424/253 |
| 4,416,892 | 11/1983 | Dawson | 424/272 |
| 4,454,138 | 6/1984 | Goring | 424/253 |
| 4,469,698 | 9/1984 | Philippossian et al. | 424/253 |
| 4,495,195 | 1/1985 | Beck et al. | 514/406 |
| 4,616,020 | 10/1986 | Furrer et al. | 514/264 |
| 4,652,654 | 3/1987 | Verga et al. | 548/217 |
| 4,684,656 | 8/1987 | Atwal | 514/274 |
| 4,684,728 | 8/1987 | Möhring et al. | 544/182 |
| 4,710,503 | 12/1987 | Hofer | 514/263 |
| 4,732,978 | 3/1988 | Kreft et al. | 546/152 |
| 4,755,517 | 7/1988 | Bruns et al. | 514/263 |
| 4,757,124 | 7/1988 | Koyanagi et al. | 526/62 |
| 4,769,377 | 9/1988 | Snyder et al. | 514/263 |
| 4,770,990 | 9/1988 | Nakamura et al. | 430/564 |
| 4,803,216 | 2/1989 | Appleton et al. | 514/407 |
| 4,810,719 | 3/1989 | Appleton et al. | 514/406 |
| 4,826,868 | 5/1989 | Wachter et al. | 514/407 |
| 4,831,152 | 5/1989 | Itoh et al. | 548/224 |
| 4,851,321 | 7/1989 | Takagi et al. | 430/264 |
| 4,868,183 | 9/1989 | Kanai et al. | 514/255 |
| 4,874,869 | 10/1989 | Ueda et al. | 548/309 |
| 4,883,801 | 11/1989 | Nathanson | 514/263 |
| 4,910,213 | 3/1990 | Imamura et al. | 514/367 |
| 4,918,074 | 4/1990 | Tsuda et al. | 514/258 |
| 4,925,847 | 5/1990 | Hofer | 514/263 |
| 4,965,169 | 10/1990 | Hirano et al. | 430/264 |
| 4,971,972 | 11/1990 | Doll et al. | 514/265 |
| 4,981,857 | 1/1991 | Daluge et al. | 514/263 |
| 4,994,363 | 2/1991 | Koya et al. | 430/564 |
| 5,010,081 | 4/1991 | Hofer | 514/263 |
| 5,047,411 | 9/1991 | Takasugi et al. | 514/300 |
| 5,057,517 | 10/1991 | Johnston et al. | 514/254 |
| 5,068,236 | 11/1991 | Suzuki et al. | 514/263 |
| 5,091,431 | 2/1992 | Tulshian et al. | 514/262 |
| 5,098,464 | 3/1992 | Barton et al. | 71/92 |
| 5,110,818 | 5/1992 | Allgeier | 514/261 |
| 5,114,835 | 5/1992 | Sakaoue | 430/393 |
| 5,116,717 | 5/1992 | Matsushita et al. | 430/264 |
| 5,117,830 | 6/1992 | McAfee et al. | 128/654 |
| 5,139,921 | 8/1992 | Takagi et al. | 430/264 |
| 5,177,074 | 1/1993 | Allen et al. | 514/234 |
| 5,190,942 | 3/1993 | Poss | 514/235.8 |
| 5,191,084 | 3/1993 | Bagli et al. | 546/279 |
| 5,202,243 | 4/1993 | Balani | 435/118 |
| 5,206,255 | 4/1993 | Ubasawa et al. | 514/374 |
| 5,264,589 | 11/1993 | Corey | 548/51 |
| 5,270,206 | 12/1993 | Saccomano | 435/280 |
| 5,288,896 | 2/1994 | Capiris et al. | 560/27 |
| 5,290,782 | 3/1994 | Suzuki et al. | 514/263 |
| 5,322,847 | 6/1994 | Marfat et al. | 514/303 |
| 5,342,835 | 8/1994 | Pepin et al. | 514/227.5 |
| 5,424,432 | 6/1995 | Fredenburgh et al. | 546/118 |
| 5,434,150 | 7/1995 | Austel et al. | 514/228.5 |
| 5,436,258 | 7/1995 | Blake et al. | 514/372 |
| 5,449,686 | 9/1995 | Christensen, IV | 514/330 |
| 5,451,596 | 9/1995 | Ullrich | 514/375 |
| 5,496,853 | 3/1996 | Shiota et al. | 514/469 |
| 5,602,157 | 2/1997 | Christensen, IV | 514/362 |
| 5,602,173 | 2/1997 | Christensen, IV | 514/474 |
| 5,631,260 | 5/1997 | Belardinelli et al. | 514/263 |
| 5,665,737 | 9/1997 | Cavalla et al. | 514/338 |

FOREIGN PATENT DOCUMENTS

| | | |
|---|---|---|
| 0191313 | 8/1986 | European Pat. Off. |
| 0203721 | 12/1986 | European Pat. Off. |
| 0256692 | 2/1988 | European Pat. Off. |
| 0258191 | 3/1988 | European Pat. Off. |
| 0343643 A2 | 11/1989 | European Pat. Off. |
| 360701 | 3/1990 | European Pat. Off. |
| 0369744 | 5/1990 | European Pat. Off. |
| 0386683 | 9/1990 | European Pat. Off. |
| 0389282 | 9/1990 | European Pat. Off. |
| 0400799 | 12/1990 | European Pat. Off. |
| 0435811 | 7/1991 | European Pat. Off. |
| 0463756 | 1/1992 | European Pat. Off. |
| 0470805 A1 | 2/1992 | European Pat. Off. |
| 0497564 A1 | 8/1992 | European Pat. Off. |
| 051865 A1 | 11/1992 | European Pat. Off. |
| 0536713 | 4/1993 | European Pat. Off. |
| 0590919 | 4/1994 | European Pat. Off. |
| 0619316 | 10/1994 | European Pat. Off. |
| 0623607 | 11/1994 | European Pat. Off. |
| 0645389 | 3/1995 | European Pat. Off. |
| 0671389 | 9/1995 | European Pat. Off. |
| 0675124 | 10/1995 | European Pat. Off. |
| 0685474 | 12/1995 | European Pat. Off. |
| 0685479 | 12/1995 | European Pat. Off. |
| 0728759 | 8/1996 | European Pat. Off. |
| 0731099 | 9/1996 | European Pat. Off. |
| 0779291 | 6/1997 | European Pat. Off. |
| 835818 | 2/1961 | France . |
| 1548252 | 12/1968 | France . |
| 2104932 | 6/1972 | France . |
| 2008464 | 9/1970 | Germany . |
| 2314676 | 10/1973 | Germany . |
| 2346034 | 4/1974 | Germany . |
| 51-54587 | 5/1976 | Japan . |
| 57-21375 | 2/1982 | Japan . |
| 559056 | 3/1993 | Japan . |
| 6211856 | 8/1994 | Japan . |
| 7118247 | 5/1995 | Japan . |
| 717952 | 7/1995 | Japan . |
| 8113567 | 5/1996 | Japan . |
| 215948 | 10/1989 | New Zealand . |
| 1077689 | 8/1967 | United Kingdom . |
| 1260793 | 1/1972 | United Kingdom . |
| 1498705 | 1/1978 | United Kingdom . |
| 1561005 | 2/1980 | United Kingdom . |
| 2041359 | 9/1980 | United Kingdom . |
| 1580782 | 12/1980 | United Kingdom . |
| 2283488 | 5/1995 | United Kingdom . |

| | | |
|---|---|---|
| 8601724 | 3/1986 | WIPO . |
| 8706576 | 4/1986 | WIPO . |
| 9631487 | 10/1986 | WIPO . |
| 9100858 | 1/1991 | WIPO . |
| 9200968 | 1/1992 | WIPO . |
| 9205175 | 4/1992 | WIPO . |
| 9205176 | 4/1992 | WIPO . |
| 9207567 | 5/1992 | WIPO . |
| 9219594 | 11/1992 | WIPO . |
| 9307111 | 4/1993 | WIPO . |
| 9307141 | 4/1993 | WIPO . |
| 9314081 | 7/1993 | WIPO . |
| 9314082 | 7/1993 | WIPO . |
| 9315044 | 8/1993 | WIPO . |
| 9315045 | 8/1993 | WIPO . |
| 9318024 | 9/1993 | WIPO . |
| 9319747 | 10/1993 | WIPO . |
| 9319749 | 10/1993 | WIPO . |
| 9319750 | 10/1993 | WIPO . |
| 9319751 | 10/1993 | WIPO . |
| 9322287 | 11/1993 | WIPO . |
| 9325517 | 12/1993 | WIPO . |
| 9402465 | 2/1994 | WIPO . |
| 9410118 | 5/1994 | WIPO . |
| 9412461 | 6/1994 | WIPO . |
| 9414742 | 7/1994 | WIPO . |
| 9414800 | 7/1994 | WIPO . |
| 9420446 | 9/1994 | WIPO . |
| 9420455 | 9/1994 | WIPO . |
| 9420460 | 9/1994 | WIPO . |
| 9422859 | 10/1994 | WIPO . |
| 9425437 | 11/1994 | WIPO . |
| 9500139 | 1/1995 | WIPO . |
| 9501338 | 1/1995 | WIPO . |
| 9503297 | 2/1995 | WIPO . |
| 9503794 | 2/1995 | WIPO . |
| 9504045 | 2/1995 | WIPO . |
| 9504046 | 2/1995 | WIPO . |
| 9508534 | 3/1995 | WIPO . |
| 9509623 | 4/1995 | WIPO . |
| 9509624 | 4/1995 | WIPO . |
| 9509627 | 4/1995 | WIPO . |
| 9509836 | 4/1995 | WIPO . |
| 9509837 | 4/1995 | WIPO . |
| 9604253 | 5/1995 | WIPO . |
| 9514667 | 6/1995 | WIPO . |
| 9517386 | 6/1995 | WIPO . |
| 9517392 | 6/1995 | WIPO . |
| 9517399 | 6/1995 | WIPO . |
| 9522520 | 8/1995 | WIPO . |
| 9523148 | 8/1995 | WIPO . |
| 9527692 | 10/1995 | WIPO . |
| 9535281 | 12/1995 | WIPO . |
| 9535282 | 12/1995 | WIPO . |
| 9535283 | 12/1995 | WIPO . |
| 9535284 | 12/1995 | WIPO . |
| 9535285 | 12/1995 | WIPO . |
| 9600215 | 1/1996 | WIPO . |
| 9603396 | 2/1996 | WIPO . |
| 9603399 | 2/1996 | WIPO . |
| 9612720 | 5/1996 | WIPO . |
| 9620157 | 7/1996 | WIPO . |
| 9620158 | 7/1996 | WIPO . |
| 9620174 | 7/1996 | WIPO . |
| 9620175 | 7/1996 | WIPO . |
| 9624350 | 8/1996 | WIPO . |
| 9631476 | 10/1996 | WIPO . |
| 9631485 | 10/1996 | WIPO . |
| 9631486 | 10/1996 | WIPO . |
| 9628430 | 11/1996 | WIPO . |
| 9636595 | 11/1996 | WIPO . |
| 9636596 | 11/1996 | WIPO . |
| 9636611 | 11/1996 | WIPO . |
| 9636624 | 11/1996 | WIPO . |
| 9636625 | 11/1996 | WIPO . |
| 9636626 | 11/1996 | WIPO . |
| 9636638 | 11/1996 | WIPO . |
| 9638150 | 12/1996 | WIPO . |
| 9703070 | 1/1997 | WIPO . |
| 9703967 | 2/1997 | WIPO . |
| 9712887 | 4/1997 | WIPO . |
| 9712888 | 4/1997 | WIPO . |
| 9720833 | 6/1997 | WIPO . |
| 9722585 | 6/1997 | WIPO . |
| 9722586 | 6/1997 | WIPO . |
| 9723457 | 7/1997 | WIPO . |
| 9723460 | 7/1997 | WIPO . |
| 9723461 | 7/1997 | WIPO . |
| 9724334 | 7/1997 | WIPO . |
| 9725312 | 7/1997 | WIPO . |
| 9728143 | 8/1997 | WIPO . |
| 9728144 | 8/1997 | WIPO . |
| 9728145 | 8/1997 | WIPO . |
| 9728146 | 8/1997 | WIPO . |
| 9728147 | 8/1997 | WIPO . |
| 9728148 | 8/1997 | WIPO . |
| 9728155 | 8/1997 | WIPO . |

OTHER PUBLICATIONS

Derwent Abstract of JP 58111034, published Jul. 1, 1983.

Ronald E. Weishaar, et al.., Subclasses of Cyclic GMP–Specific phosphodiesterase and their role in regulating the effects of atrial natriuretic factor, Dept. Of Pharmacology, Parke–Davis Pharmaceutical Research Division, Warner–Lambert Co. Hypertension, vol. 15, No. 5, May 1990.

"Differential modulation of tissue function and therapeutic potential selective inhibitors of cyclic nucleotide phosphodiesterase isoenzymes", C. David Nicholson, R.A. John Chaliss and Mohammed Shahid, 1991, Elsevier Science Publishers Ltd. (UK), TIPS 12:19–27.

"Phosphodiesterase inhibiots: new opportunities for the treatment of asthma", Theodore J. Torphy, Bradley J. Undem, *Thorax* 1991; 46:512–523.

"Novel phosphodiesterase inhibitors for the therapy of asthma", Theodore J. Torphy, George P. Livi and Siegfried B. Christensen, DN&P 6(4), May 1993 pp. 203–214.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, pp. 69–92.

"Identification characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W.P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future, 1992, 17(9):799–807.

"Could isoenzyme–selective phosphodiesterase inhibitors render bronchodilator therapy redundant in the treatment of bronchial asthma?", Mark A. Giembycz, Biochemical Pharmacology, 1992, vol. 43, No. 10 pp. 2041–2051.

"Differential pharmacologic sensitivity of cyclic nucleotide phosphodiesterase isozymes from cardiac muscle, arterial and airway smooth muscle", Paul J. Silver, Linda T. Hamel, Mark H. Perrone, Ross G. Bently, Cynthia R. Bushover and Dale B. Evans, European Journal of Pharmacology, 150 (1988) 85–94, Elsevier.

"The pharmacology and therapeutic use of theophylline", Miles Weinberger, M.D., The Journal of Allergy and Clinical Immunology, vol. 73, No. 5, Part 1, 525–544, 1984.

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

Chemical Abstracts, vol. 85, No. 1 (Jul. 5, 1976) 5692s (Enoki).

Chemical Abstracts, vol. 84, No. 25 (Jun. 21, 1976) 180299v (Enoki).

Chemical Abstracts, vol. 86, No. 7 (Feb. 14, 1977) 43746r (Aida).

Isomura et al., "Studies of the synthesis and anti–inflammatory activity of 2,6–Di–tert–butylphenols with a heterocyclic group at the 4–position.I", vol. 31, No. 9, pp. 3168–3178 (1983).

Chemical Abstracts 103: 37354, 1985 (Nagarajan).

Chemical Abstracts 116: 255335, 1992 (Bender).

Itaya, *Tetrahedron Letters*, vol. 23, No. 21 (1982), pp. 2203–2204.

Reitz, *Journal of Organic Chemistry*, vol. 55, No. 22 (Oct. 26, 1990), pp. 5761–5766.

Chemical Abstracts 88: 51054, 1977 (Ninomiya).

Chemical Abstracts, vol. 82 (19) May 12, 1975, Abstract #125358x (Kazimierezuk).

Chemical Abstracts 114: 246982, 1990 (Naruto).

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Chemical Abstracts 92: 6207, 1977 (Pirisino).

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

G.T. Rogers and T.L.V. Ulbricht, Synthesis of 3–Methylisoguanine (6–amino–3–methylpurin–2(3H)–one), J. Chem. Soc. (C), pp. 2364–2366 1971.

Chemical Abstracts 116:173873 (1979) Girshovich.

J. A. Montgomery, et al., "Synthesis of Potential Anticancer Agents. XIX. 2–Substituted $N^6$–Alkyladenines" (1959) J.A.C.S. vol. 81, pp. 3963–3967.

Chemical Abstracts 53:6243 (1957) Elion.

T. Fuji, et al. "3–Substituted Adenines. In Vitro Enzyme Inhibition and Antiviral Activity",(1979) Journal of Medicinal Chemistry, vol. 22, No. 2, pp. 126–129.

Burger, Ed. "Medicinal Chemistry" 2d ed. pp. 42–43, Interscience, New York, New York (1960).

Ram et al., Indian J. Chem., Sect. B (1993), 32B(9), 924–8.

Salem et al., CA 117:26410 (1992).

Ram et al., CA 116:6463 (1991).

Nikolyukin et al., CA 114:122145 (1990).

Pepin et al., CA 114;96801 (1990).

Murray et al., CA 12:198208 (1989).

Agrawal, CA 109:54701 (1987).

Tominaga et al., CA 107:236648 (1987).

Vishwakarma et al., CA 104:168404 (1985).

Reddy et al., CA 104:168228 (1985).

Feeny, CA 92:17174 (1979).

De Lucia et al., CA 68:96797 (1968).

Derwent Abstract of JP 1200246, published Aug. 11, 1989.

Derwent Abstract of JP 1245256, published Sep. 29, 1989.

Derwent Abstract of JP 1231049, published Sep. 14, 1989.

Derwent Abstract of JP 1229251, published Sep. 12, 1989.

Derwent Abstract of JP 1225951, published Sep. 8, 1989.

Derwent Abstract of JP 1224756, published Sep. 7, 1989.

Derwent Abstract of JP 1224755, published Sep. 7, 1989.

Derwent Abstract of JP 1219748, published Sep. 1, 1989.

Derwent Abstract of JP 1216353, published Aug. 20, 1989.

Derwent Abstract of JP 1214845, published Aug. 29, 1989.

Derwent Abstract of JP 1093733, published Apr. 12, 1989.

Derwent Abstract of JP 63271246, publised Nov. 9, 1988.

Derwent Abstract of DE 1445519, published Jan. 16, 1969.

CA Select: "Anti–inflammatory Agents & Arthritis" Issue 7, 1996, p. 26.

Abstract of PCT Gazette—Section I, No. 26/19 of WO 96/16657 Jun. 6, 1996.

Abstract of JP 6–192244 (1 page) Jul. 12, 1994.

CA of "1–Pharmacology", vol. 106, 1987, p. 61.

CA Selects: "Allergy & Antiallergic Agents", Issue 5, 1996, pp. 17 and 19.

CA Selects: "Allergy & Antiallergic Agents", Issue 21, 1995, p. 13.

CA Selects: Anti–Inflammatory Agents & Arthritis, Issue 23, 1995, p. 17 and 23.

CA Selects: "Anti–Inflammatory Agents & Arthritis", Issue 25, 1996, (1 page).

CA 171494, 171495 and KG–2683 of Annual Drug Data Report 1991 (1 sheet).

Derwent Abstract of DE4309969 Mar. 26, 1993.

2-HETEROARYL AND 2-HETEROCYCLIC BENZOXAZOLES AS PDE IV INHIBITORS FOR THE TREATMENT OF ASTHMA

This application is a continuation-in-part of U.S. Ser. No. 08/833,897, filed Apr. 10, 1997, now abandoned, which is continuation of PCT/US95/14399, filed Oct. 11, 1995.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Perspectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

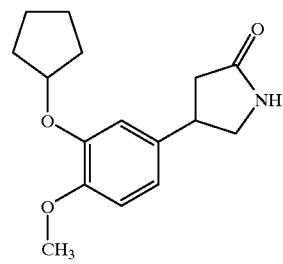

and of RO-20-1724, which has the following structural formula (B):

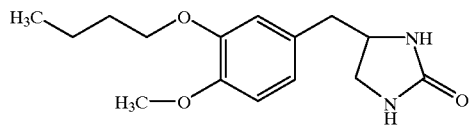

have been studied.

U.S. Pat. No. 4,308,278 discloses compounds of the Formula (C):

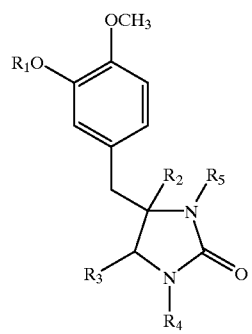

wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

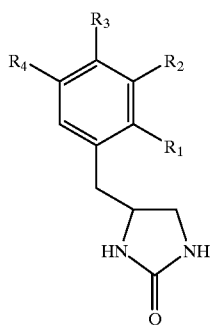

Substituents $R_1$–$R_4$ in Formula D represent a variety of groups, including hydrogen and lower alkyl.

PCT publication WO 87/06576 discloses antidepressants of Formula (E):

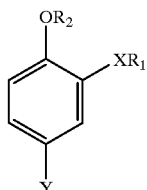

wherein $R_1$ is a polycycloalkyl group having from 7 to 11 carbon atoms; $R_2$ is methyl or ethyl; X is O or NH; and Y comprises a mono-or bicyclic heterocyclic group with optional substituents.

Rolipram, which was initially studied because of its activity as an antidepressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

SUMMARY OF THE INVENTION

The present invention is directed to compounds having the general formula (I):

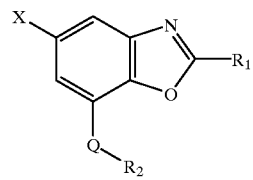

wherein:

X is a halogen;

Q is —$CH_2$—$CH_2$—, —$CH_2$—, a single or a double bond, or —$NR_1$—;

$R_1$ is a $C_{3-7}$ monocyclic ring structure containing at least one carbon atom and comprising one or more chalcogen atoms selected from the group consisting of nitrogen, sulfur and oxygen, wherein the monocyclic ring may be unsaturated, partially unsaturated or saturated, and may be unsubstituted or substituted with alkyl, cycloalkyl, alkoxy, cycloalkoxy, hydroxy or halogen; or is a bicyclic system, comprised of a phenyl ring fused to a monocyclic ring system as defined above, or comprised of two fused monocyclic ring systems as defined above, each ring containing at least one carbon atom and comprising one or more chalcogen atoms selected from the group consisting of nitrogen, sulfur and oxygen, wherein the monocyclic ring may be unsaturated, partially unsaturated or saturated, and may be unsubstituted or substituted with alkyl, cycloalkyl, alkoxy, cycloalkoxy, hydroxy or halogen.

$R_2$ is a phenyl group or a $C_{3-7}$ monocyclic ring structure as defined above, containing at least one carbon atom and comprising one or more chalcogen atoms selected from the group consisting of nitrogen, sulfur and oxygen, wherein the monocyclic ring may be unsaturated, partially unsaturated or saturated, and may be unsubstituted or substituted with alkyl, cycloalkyl, alkoxy, cycloalkoxy, hydroxy or halogen.

The present invention is also related to methods of using compounds of formula (I) for treating patients who can benefit from a modification of PDE IV levels in their bodies.

Methods of making compounds of formula (I) are also described by the present invention.

The invention is also related to a method of treating mammals with the above compounds.

DETAILED DESCRIPTION OF THE INVENTION

The present invention is directed to compounds having the general formula (I):

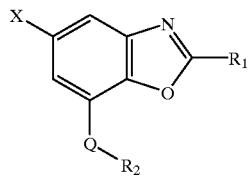

wherein:

X is a halogen;

Q is —$CH_2$—$CH_2$—, —$CH_2$—, a single or a double bond, or —$NR_1$—;

$R_1$ is a monocyclic or bicyclic ring structure, as defined below;

$R_2$ is a phenyl group or a C3-7 monocyclic ring structure as defined below.

As referred to herein, a "monocyclic ring structure" encompasses a $C_{3-4}$ monocyclic ring containing at least one carbon atom and comprising one or more chalcogen atoms selected from the group consisting of nitrogen, sulfur and oxygen, wherein the monocyclic ring may be unsaturated, partially unsaturated or saturated, and may be unsubstituted or substituted with alkyl, cycloalkyl, alkoxy, cycloalkoxy, hydroxy or halogen. Examples of unsubstituted ring monocyclic structures as defined herein include pyrrole, furan, thiophene, thiadiazole, indole, isoxazole, imidazole, oxazole, thiazole, pyrazine, pyrazole, 3-pyrroline, pyrrolidine, pyridine, and pyrimidine, among others readily apparent to those skilled in the art.

As referred to herein, a "bicyclic ring system" encompasses a phenyl ring fused to a monocyclic ring structure as defined above, containing at least one carbon atom and comprising one or more chalcogen atoms selected from the group consisting of nitrogen, sulfur and oxygen, wherein the monocyclic ring may be unsaturated, partially unsaturated or saturated, and may be unsubstituted or substituted with alkyl, cycloalkyl, alkoxy, cycloalkoxy, hydroxy or halogen, or is comprised of two fused monocyclic ring structures, each ring as defined above containing at least one carbon atom and comprising one or more chalcogen atoms selected from the group consisting of nitrogen, sulfur and oxygen, wherein each monocyclic ring may be unsaturated, partially unsaturated or saturated, and may be unsubstituted or substituted with alkyl, cycloalkyl, alkoxy, cycloalkoxy, hydroxy or halogen. Examples of unsubstituted bicyclic ring structures as defined herein are benzothiophene, benzotriazole, indole, purines, quinolines, isoquinolines, quinoxalines and carbazole, among others readily apparent to those of ordinary skill in the art.

As referred to herein, alkoxy groups encompass groups having the formula —OR where R includes $C_1$ to $C_8$ alkyl which can be branched or straight chain alkyl or cycloalkyl.

The present invention also includes organic and inorganic salts, hydrates, esters, prodrugs and metabolites of the compounds of formula I.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

Compounds falling into the genus of PDE IV inhibitors of the present invention include:

5-chloro-2-(furan-2-yl)-7-[2-(pyridin-2-yl)ethyl]-benzoxazole;
5-chloro-2-(pyridin-4-yl)-7-[2-(pyridin-2-yl)ethyl]-benzoxazole;
5-chloro-7-[2-(pyridin-2-yl)ethyl]-2-(thien-2-yl)-benzoxazole;
5-chloro-7-[2-(pyridin-2-yl)ethyl]-2-(thien-3-yl)-benzoxazole;
2-(benzo[b]thien-2-yl)-5-chloro-7-[2-(pyridin-2-yl)ethyl]-benzoxazole;
2-(isoquinolin-1-yl)-5-chloro-7-[2-(pyridin-2-yl)ethyl]-benzoxazole;
5-chloro-2-[4-methyl-(1,2,3-thiadiazol-5-yl)]-7-[2-(pyridin-2-yl)ethyl]-benzoxazole;
5-chloro-7-[2-(pyridin-2-yl)ethyl]-2-(quinoxalin-2-yl)-benzoxazole;
5-chloro-2-(pyrazin-2-yl)-7-[2-(pyridin-2-yl)ethyl]-benzoxazole;
5-chloro-2-(isoxazol-5-yl)-7-[2-(pyridin-2-yl)ethyl]-benzoxazole;
5-chloro-2-(3-methyl-pyrazol-5-yl)-7-[2-(pyridin-2-yl)ethyl]-benzoxazole;
2-(benzotriazol-5-yl)-5-chloro-7-[2-(pyridin-2-yl)ethyl]-benzoxazole;
5-chloro-2-(5-methoxyindol-2-yl)-7-[2-(pyridin-2-yl)ethyl]-benzoxazole;
5-chloro-2-(1-methylpyrrol-2-yl)-7-[2-(pyridin-2-yl)ethyl]-benzoxazole;
5-chloro-7-[2-(pyridin-2-yl)ethyl]-2-(quinolin-8-yl)-benzoxazole;
5-chloro-2-(5-fluoroindol-2-yl)-7-[2-(pyridin-2-yl)ethyl]-benzoxazole;
5-chloro-2-(imidazol-5-yl)-7-[2-(pyridin-2-yl)ethyl]-benzoxazole;
5-chloro-2-(pyrazol-4-yl)-7-[2-(pyridin-2-yl)ethyl]-benzoxazole;
5-chloro-2-(furan-3-yl)-7-[2-(pyridin-2-yl)ethyl]-benzoxazole;
5-chloro-2-(2,4-dimethyl-furan-3-yl)-7-[2-(pyridin-2-yl)ethyl]-benzoxazole; and
5-chloro-7-[2-(pyridin-2-yl)ethyl]-2-(tetrahydrofuran-3-yl)-benzoxazole.

The compounds of the present invention can be synthesized by many routes. It is well known in the art of organic synthesis that many different synthetic protocols can be used to prepare a given compound. Different routes can involve more or less expensive reagents, easier or more difficult separation or purification procedures, straightforward or cumbersome scale-up, and higher or lower yield. The skilled synthetic organic chemist knows well how to balance the competing characteristics of synthetic strategies. Thus the compounds of the present invention are not limited by the choice of synthetic strategy, and any synthetic strategy that yields the compounds described above can be used.

In order to exemplify methods of making and using compounds according to the present invention, the following examples are provided without any intent to limit the scope of the instant invention to the discussion therein. All part and percentages are by weight unless otherwise indicated. The following abbreviations are used in the discussion of the examples: "DMF" is N,N-dimethylformamide; "THF" is tetrahydrofuran; "Tol" is tolyl; "Et$_2$O" is diethyl ether; "OAc" is acetate; "AcOH" is acetic acid; "Het" is a heterocyclic group; "Ph" is phenyl; "Me" is methyl; "EtOAc" is ethyl acetate; "DCM" is dichloromethane; "RT" is room temperature; and "TLC" is thin layer chromatography.

2-heteroaryl and 2-heterocyclic benzoxazoles of the present invention may be prepared according to the following general reaction scheme 1.

Scheme 1

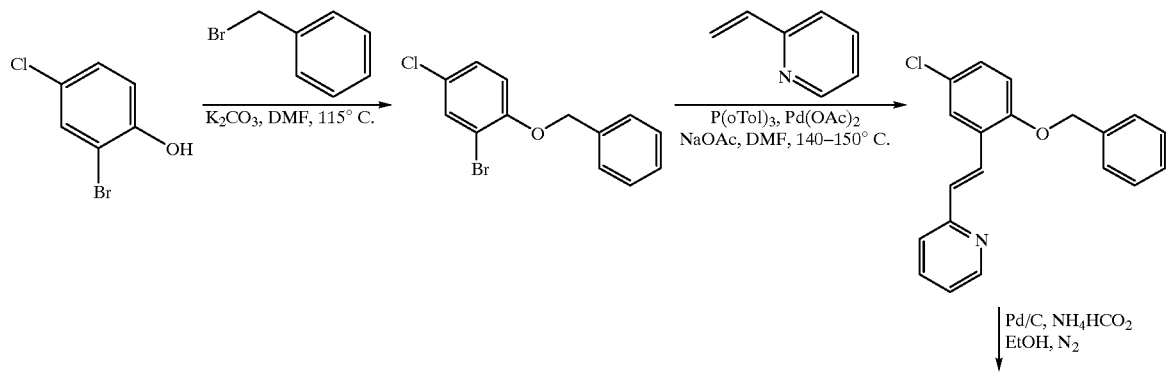

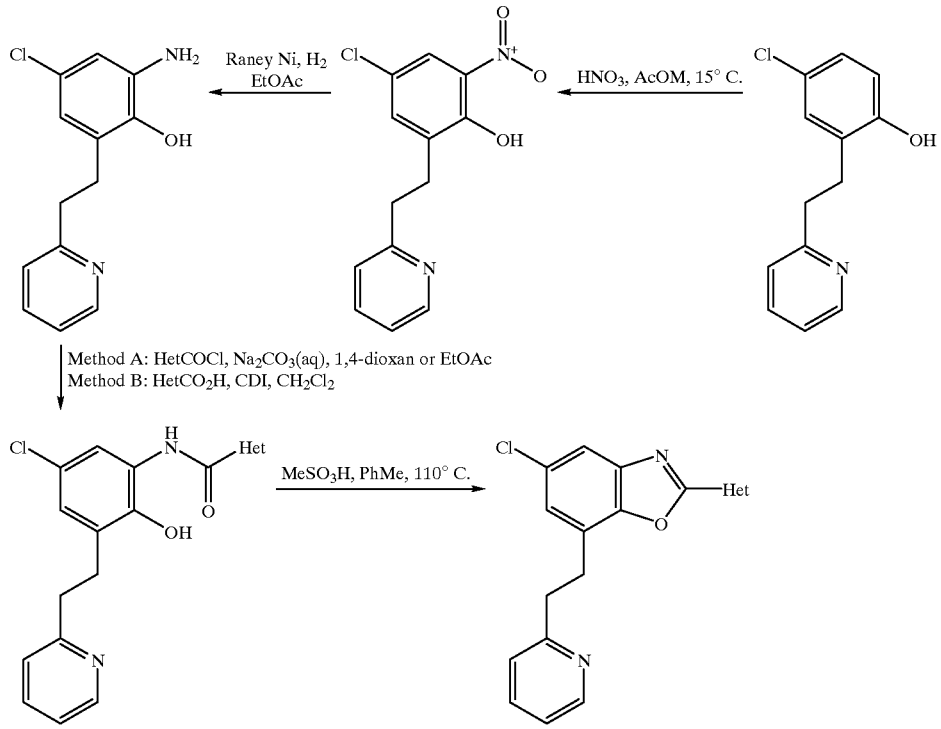

DETAILED DESCRIPTION OF PREFERRED EMBODIMENTS

The following examples illustrate various aspects of the present invention.

Preparation of Intermediates
Preparation of 2-bromo-4-chlorobenzyloxybenzene 18.2 g (0.13 mol.) of potassium carbonate and 18.74 g (13.03 ml, 0.11 mol.) benzyl bromide is added to 2-bromo-4-chlorophenol (1) (25 g, 0. 12mol) in DMF (25 ml) under nitrogen. The reaction mixture is heated (oil bath temperature 115° C.) for 1.5 hours and then allowed to cool and left to stand overnight at RT. The reaction mixture is diluted with distilled water (100 ml) and then extracted with Et$_2$O (2×100 ml). The organic extracts are combined, washed with 1M sodium hydroxide (100 ml) and concentrated in vacuo to leave a colorless oil. This oil is purified by flash chromatography (SiO$_2$, pentane) to yield a colorless oil which crystallised on standing to give the title compound as a colorless solid, (29.14 g, 81%), m.p. 49–50.5° C. δ$_H$ (250 MHz, CDCl$_3$), 7.55 (d, J=2.6 Hz, 1H), 7.46 (m, 5H), 7.19 (dd, J=8.9, 2.5 Hz, 1H), 6.84 (d, J=8.8 Hz, 1H), 5.13 (s, 2H).
Preparation of 4-chloro-2-[2-(pyridin-2-yl)vinyl]benzyloxybenzene 124.4 g (417.8 mmol) of 2-Bromo-4-chlorobenzyloxybenzene, 54.8 ml (501.4 mmol) of 2-vinylpyridine, 4.69 g (20.9 mmol) palladium acetate, 25.4 g (83.6 mmol) tritolylphosphine, and 48 g (584.9 mmol) sodium acetate are heated together in 200 ml DMF at 165° C. (oil bath temperature) under nitrogen for 8 hours. The cooled mixture is evaporated to dryness in vacuo. The residue is then diluted with Et$_2$O:DCM (3:1, 1 L) and washed with sodium carbonate solution (1M, 3×1 L). The aqueous washings are extracted with Et$_2$O:DCM (3:1, 1L) and the combined organic extract dried using MgSO$_4$, filtered through celite, and evaporated to dryness to leave an orange solid. Flash chromatography (SiO$_2$, DCM:pentane 3:1) gave a yellow solid which was triturated with pentane (600 ml) to give the title compound as a pale yellow solid (77.5 g, 58%), m.p. 105.2–105.8° C. δH (250 MHz, CDCl$_3$) 8.60 (d, J=4.5 Hz, 1H), 7.96 (d, J=16.3 Hz, 1H), 7.64–7.60 (m, 2H), 7.46–7.34 (m, 7H), 7.24 (d, J=16.6 Hz, 1H), 7.18–7.11 (m, 1H), 6.95 (d, J=8.9 Hz, 1H), 5.16 (s, 2H).
Preparation of 4-chloro-2-[2-(pyridin-2-yl)ethyl]phenol To a solution of 24.0 g (74.57 mmol) 4-chloro-2-[2-(pyridin-2-yl)vinyl]-phenol in 400 ml ethanol is added 1.0 g palladium on charcoal 10% followed by 23.5 g (373 mmol) ammonium formate. The reaction mixture is then heated in an oil bath at 60° C. for 6 hours under a nitrogen atmosphere. The reaction mixture is filtered through celite, and the filtrate evaporated in vacuo to leave a colorless solid. Distilled water is added to the residue, which is extracted with 500 ml and then 300 ml DCM. The organic extracts were dried using MgSO$_4$ and concentrated in vacuo to give the title compound as a colourless solid (15.81 g, 91%), m.p. 135–137° C. δ$_H$ (250 MHz, CDCl$_3$) 8.52–8.49 (dd, J=5.8,1.7 Hz, 1H), 7.65 (dt, J=7.8,1.7 Hz, 1H), 7.26–7.17 (m, 2H) 7.11 (d, J=2.6 Hz, 1H), 7.04 (dd, J=8.6, 2.6 Hz, 1H), 6.81 (d, J=8.6 Hz, 1H), 3.31–3.26 (m, 2H), 3.10–3.05 (m, 2H).
Preparation of 4-chloro-2-nitro-6-[2-(pyridin-2-yl)ethyl]phenol To a solution of 12.5 g (54.56 mmol) 4-chloro-2-[2-(pyridin-2-yl)ethyl]phenol in 80 ml acetic acid is added portionwise to a nitrating mixture of 70% nitric acid (8.59 g, 136.39 mmol) in 20 ml acetic acid at 5–10° C. The reaction mixture is left to stir at this temperature for 2.5 hours. The pH of the reaction mixture is then adjusted to pH 5.5–6.0 (pH meter) by the addition of a saturated solution of sodium carbonate. The resulting reaction mixture is then extracted with EtOAc (3×300 ml). Concentration of the organic extracts in vacuo yielded a brown oil. This oil is purified by flash chromatography (SiO$_2$, 30% EtOAc in hexane) to give the title compound as a yellow solid, (12.48 g, 82%), m.p. 97–100° C. δ$_H$ (250 MHz, CDCl$_3$), 11.1 (bs, 1H), 8.57–8.55 (m, 1H), 7.94 (d, J=2.6 Hz, 1H), 7.60 (dt, J=7.7,1.7 Hz, 1H), 7.35 (d, J=2.5 Hz, 1H), 7.17–7.11 (m, 2H), 3.21–3.08 (m, 4H).

Preparation of 2-amino-4-chloro-6-[2-(pyridin-2-yl)ethyl] phenol

To a vigorously stirred suspension of Raney Nickel (3.5 g of a 50% slurry in water, washed with ethanol then EtOAc) in EtOAc (20 ml) is added 4-chloro-2-nitro-6-[2-(pyridin-2-yl)ethyl]phenol (2.09 g, 7.50 mmole) in EtOAc (10 ml). The solution is stirred vigorously overnight under an atmosphere of hydrogen. After this time no starting material is visible by TLC analysis. The solution is decanted from the Raney Nickel. The Raney Nickel was washed several times with EtOAc and the washings combined with the reaction mixture solution. Concentration in vacuo yielded a brown oil which is purified by flash chromatography (SiO$_2$; 30% EtOAc in hexane) to yield a pale orange oil (1.88 g, 100%). This was recrystallised from EtOAc/pentane to give the title compound as a pale yellow crystalline solid (1.55 g, 83%), m.p. 91–92° C. dH (250 MHz, CDCl$_3$) 11.5 (bs, 1H), 8.49 (dd, J=5.6, 2.0 Hz, 1H), 7.63 (dt, J=7.7, 1.7 Hz, 1H ), 7.20–7.16 (m, 2H), 6.54 (d, J=2.5 Hz, 2H), 3.84 (bs, 2H ), 3.30–3.25 (m, 2H ), 3.06–3.02 (m, 2H).

Preparation of the 2-heteroaryl-benzoxazoles

EXAMPLE 1

General Method A, Exemplified by Preparation of 5-chloro-2-(furan-2-yl)-7-[2-(pyridin-2-yl)ethyl]-benzoxazole 0.24 ml of 2-furoyl chloride (2.41 mmol) is dropwise added to a mixture of 200 mg (0.8 mmol) 2-amino-4-chloro-6-[2-(pyridin-2-yl)ethyl]phenol, 10 ml EtOAc, and 10 ml saturated sodium bicarbonate. The reaction mixture is stirred at RT for 2 hours, then diluted with 30 ml water. The aqueous phase is extracted with EtOAc (3×100 ml). The combined organic phases are then washed with brine (40 ml), dried using MgSO$_4$, filtered and concentrated in vacuo to give the intermediate amide as a white solid (330 mg; crude yield 105%). δ$_H$ (300 MHz, CDCl$_3$) 8.55 (m, 1H), 8.28 (d, 1H), 7.75 (s, 1H), 7.60 (t, 1H), 7.55 (d, 1H), 7.35 (s, 1H), 7.20 (m, 1H), 7.15 (d, 1H), 7.13 (d, 1H), 6.70 (d, 1H), 6.50 (m, 1H), 3.35–3.00 (m, 4H).

A 50 ml single neck round bottomed flask is charged with 330 mg (0.8 mmol) crude amide, 20 ml toluene, and 0.18 ml (2.76 mmol) methanesulphonic acid and heated at reflux for 8 hours with a Dean-Stark trap attached for the removal of water by azeotrope. The cooled reaction mixture is treated with triethylamine (0.5 ml), diluted with DCM (100 ml), washed with water (2×50 ml), brine (2×50 ml), treated with decolorising carbon, dried using Na$_2$SO$_4$, filtered and concentrated in vacuo. The crude product is purified by chromatography (SiO$_2$, 50 g, 20% EtOAc: hexanes) to provide the title compound as a white crystalline solid (78 mg, 30%), m.p. 112°–114° C. δ$_H$ (300 MHz, CDCl$_3$) 8.59 (d, 1H), 7.68 (s, 1H), 7.55 (m, 2H), 7.25 (s, 1H), 7.15 (s, 1H), 7.06 (m, 2H), 6.62 (m, 1H), 3.39–3.21 (m, 4H).

EXAMPLE 2

General Method B, Exemplified by Preparation of 5-chloro-2-(pyridin-4-yl)-7-[2-(pyridin-2-yl)ethyl]-benzoxazole 0.39 g (2.41 mmol) of 1,1'-carbonyldiimidazole is added to a stirred solution of 0.30 g (2.41 mmol) isonicotinic acid in 10 ml DCM. On addition of the 1,1'-carbonyl-diimidazole an exotherm is observed. The reaction is followed by TLC analysis (10% DCM:MeOH) until no further reaction is observed. After this time 0.50 g (2.01 mmol) 6-amino-4-chloro-2-[2-(pyridin-2-yl)ethyl)] phenol is added and the mixture is stirred for 24 hours at RT. The reaction mixture is evaporated to dryness in vacuo to give a brown oil. This oil is dissolved in EtOAc (50ml) and washed successively with sodium hydroxide (0.5M, 50 ml), brine (50 ml) and water (50 ml). The organic phase is separated, dried (MgSO$_4$) and evaporated to dryness in vacuo to give the amide/ester intermediate (0.44 g) as an orange solid.

To a stirred solution of the 0.44 g (1.24 mmol) amide/ester mixture in 10 ml toluene is added 0.20 ml (3.04 mmol) methanesulphonic acid and ca 0.5 g MgSO$_4$. The reaction mixture is then heated at reflux for 24 hours. The mixture is cooled to RT and concentrated to dryness in-vacuo. The residue is diluted with 50 ml EtOAc and washed successively with 50 ml saturated sodium bicarbonate solution and 50 ml water, and dried using MgSO$_4$. The solvent is next evaporated to dryness in vacuo. The residue is purified by flash chromatography (SiO2; 30% EtOAc:pentane) followed by recrystallisation from EtOAc:pentane to give the title compound as a pale orange fluffy solid (0.1 g, 24%). TLC (SiO$_2$, EtOAc:hexanes 1:1, Rf=0.27). 8H (250 MHz, CDCl$_3$) 8.84 (dd, J=4.82, 1.64 Hz, 1H), 8.58 (dd, J=4.74, 1.62 Hz, 1H), 8.31 (dt, J=4.74, 1.62 Hz, 1H), 7.91 (dt, J=7.76, 1.7 Hz, 1H), 7.65 (d, J=2.01 Hz, 1H), 7.57 (dt, J=7.65, 1.83 Hz, 1H), 7.48 (ddd, J=7.63, 4.78, 1.13 Hz, 1H), 7.19 (d, J=2.02 Hz, 1H), 7.15–7.08 (m, 2H), 3.44 (m, 2H), 3.28 (m, 2H).

EXAMPLE 3

Preparation of 5-chloro-7-[2-(pyridin-2-yl)ethyl]-2-(thien-2-yl)-benzoxazole

This compound is prepared from 2-amino-4-chloro-6-[2-(pyridin-2-yl)ethyl]phenol and 2-thienyl chloride using method A, with ethyl acetate as solvent to give the crude amide in 99% yield. This is treated with methanesulphonic acid in toluene at reflux, with azeotropic removal of water to give the title compound, (31%) as a white crystalline solid after trituration and recrystallisation (EtOAc), m.p. 90–91° C. TLC (SiO$_2$; EtOAc:hexanes 1:1, Rf=0.46). Mass Spectrum CI (methane), m/z=341 [M+H]$^+$.

EXAMPLE 4

Preparation of 5-chloro-7-[2-(pyridin-2-yl)ethyl]-2-(thien-3-yl)-benzoxazole

This compound is prepared from 2-amino-4-chloro-6-[2-(pyridin-2-yl)ethyl]phenol, and 3-thienyl chloride using method A with 1,4-dioxan as solvent to give the crude amide in a 100% yield. This is treated with methanesulphonic acid in toluene at reflux, with azeotropic removal of water. Purification by flash chromatography (SiO$_2$, EtOAc:hexanes 1:1), gave the title compound, (30%) as a white crystalline solid, m.p. 126–127° C. TLC (SiO$_2$, EtOAc:hexanes 1:1, Rf=0.46). CI Mass Spectrum (methane), m/z=341 [M+H]$^+$.

EXAMPLE 5

Preparation of 2-(benzo[b]thien-2-yl)-5-chloro-7-[2-(pyridin-2-yl)ethyl]-benzoxazole This compound is prepared from 2-amino-4-chloro-6-[2-(pyridin-2-yl)ethyl]-phenol and benzo[b]thiophene-2-carbonyl chloride using method A with 1,4-dioxan as solvent to give the crude amide (73%). This is treated with methanesulphonic acid in toluene at reflux with azeotropic removal of water to give the title compound, (41%) as a white crystalline solid m.p.=183–184° C. TLC (SiO$_2$, EtOAc:hexanes 1:1, Rf=0.56). CI Mass Spectrum (methane) m/z=391 [M+H]$^+$.

EXAMPLE 6
Preparation of 2-(isoquinolin-1-yl)-5-chloro-7-[2-(pyridin-2-yl)ethyl]-benzoxazole This is prepared from 2-amino-4-chloro-6-[2-(pyridin-2-yl)ethyl]phenol and isoquinoline-1-carboxylic acid using method B, to give an intermediate amide (17%). This is treated with methanesulphonic acid in toluene at reflux with azeotropic removal of water to give the title compound (87%) as a white crystalline solid, m.p. 142–143° C. TLC (SiO$_2$, EtOAc:hexanes 1:1, Rf=0.13). Mass Spectrum CI (methane) m/z=386 [M+H]$^+$.

EXAMPLE 7
Preparation of 5-chloro-2-[4-methyl-(1,2,3-thiadiazol-5-yl)]-7-[2-(pyridin-2-yl)ethyl]-benzoxazole This is prepared from 2-amino-4-chloro-6-[2-(pyridin-2-yl)ethyl]phenol and 4-methyl-1,2,3-thiadiazole-5-carbonyl chloride using method A with 1,4-dioxan as solvent to give the intermediate amide (65%). This is cyclised using methanesulphonic acid in toluene with azeotropic removal of water with a Dean-Stark trap to give the title compound as a pale yellow crystalline solid (46%), m.p. 128–130° C. TLC (SiO$_2$, EtOAc:hexanes 1:1, Rf=0.55). Mass spectrum CI (methane) m/z=357 [M+H]$^+$.

EXAMPLE 8
Preparation of 5-chloro-7-[2-(pyridin-2-yl)ethyl]-2-(quinoxalin-2-yl)-benzoxazole This is prepared from 2-amino-4-chloro-6-[2-(pyridin-2-yl)ethyl]phenol and 2-quinoxaline carboxylic acid using method B to give the intermediate amide (32%). This is cyclised with methanesulphonic acid in toluene with azeotropic removal of water with a Dean-Stark trap to give the title compound as a white crystalline solid (9%), m.p 182–183° C. TLC (SiO$_2$, EtOAc:hexanes 1:1, Rf=0.27). Mass spectrum CI (methane) m/z=387 [M+H]$^+$.

EXAMPLE 9
Preparation of 5-chloro-7-[2-(pyridin-2-yl)ethyl]-2-(quinolin-3-yl)-benzoxazole This is prepared from 2-amino-4-chloro-6-[2-(pyridin-2-yl)ethyl] phenol and 3-quinoline carbonyl chloride using method A with EtOAc as solvent to give intermediate amide in 99% yield. This is cyclised with methanesulphonic acid in toluene at reflux under standard conditions to give the title compound (35%), m.p. 124–125° C. TLC (SiO$_2$, EtOAc:hexanes 1:1, Rf=0.22). Mass spectrum CI (methane) m/z=386 [M+H]$^+$.

EXAMPLE 10
Preparation of 5-chloro-2-(pyrazin-2-yl)-7-[2-(pyridin-2-yl)ethyl]-benzoxazole This is prepared from 2-amino-4-chloro-6-[2-(pyridin-2-yl)ethyl]phenol and pyrazine-2-carboxylic acid using method B with 1,4-dioxan as solvent to give the intermediate amide (58%). This is cyclised using methanesulphonic acid in refluxing toluene under standard conditions to give the title compound (35%), as a white crystalline solid, m.p. 160–161° C. TLC (SiO$_2$, EtOAc:hexanes 1:1, Rf=0.09). Mass spectrum CI (methane) m/z=337 [M+H]$^+$.

EXAMPLE 11
Preparation of 5-chloro-2-(isoxazol-5-yl)-7-[2-(pyridin-2-yl)ethyl]-benzoxazole This is prepared from 2-amino-4-chloro-6-[2-(pyridin-2-yl)ethyl]phenol and isoxazole-5-carbonyl chloride using method A with 1,4-dioxan as solvent to give the intermediate amide (65%). This is cyclised with methanesulphonic acid in toluene at reflux under standard conditions to give the title compound (46%) as a white crystalline solid m.p. 109–112° C. TLC (SiO$_2$, EtOAc:hexanes 1:1, Rf=0.30). Mass spectrum CI (methane) m/z=326 [M+H]$^+$.

EXAMPLE 12
Preparation of 5-chloro-2-(3-methyl-pyrazol-5-yl)-7-[2-(pyridin-2-yl)ethyl]-benzoxazole This is prepared from 2-amino-4-chloro-6-[2-(pyridin-2-yl)ethyl]phenol and 1-tert-butyl-3-methylpyrazole-5-carbonyl chloride using method A with 1,4-dioxan as solvent to give the intermediate amide (93%). This is cyclised with methanesulphonic acid in toluene at reflux under standard conditions to give the title compound, (4%) as a yellow solid m.p. 205–220° C. TLC (SiO$_2$, chloroform:methanol 9:1, Rf=0.65). Mass spectrum CI (methane) m/z=339 [M+H]$^+$.

EXAMPLE 13
Preparation of 2-(benzotriazol-5-yl)-5-chloro-7-[2-(pyridin-2-yl)ethyl]-benzoxazole This is prepared from 2-amino-4-chloro-6-[2-(pyridin-2-yl)ethyl]-phenol and benzotriazole-5-carbonyl chloride (prepared from the corresponding carboxylic acid with oxalyl chloride) using method A with 1,4-dioxan as solvent to give the intermediate amide (63%). This is cyclised using methanesulphonic acid in toluene at reflux under standard conditions to give the title compound as a yellow solid m.p. 242–244° C. TLC (SiO$_2$, chloroform:methanol 9:1, Rf=0.75). Mass spectrum CI (methanol) m/z=376 [M+H]$^+$.

EXAMPLE 14
Preparation of 5-chloro-2-(5-methoxyindol-2-yl)-7-[2-(pyridin-2-yl)ethyl]-benzoxazole This is prepared from 2-amino-4-chloro-6-[2-(pyridin-2-yl)ethyl] phenol and 5-methoxyindole-2-carbonyl chloride (prepared by reaction of the corresponding carboxylic acid with oxalyl chloride) using method A with 1,4-dioxan as solvent to give the intermediate amide (118%, crude). This is cyclised with methanesulphonic acid in toluene at reflux under standard conditions to give the title compound (7%) as a brown oil. TLC (SiO$_2$, hexanes:EtOAc 2:1, Rf=0.42). Mass spectrum CI (methane) m/z=404 [M+H]$^+$.

EXAMPLE 15
Preparation of 5-chloro-2-(1-methylpyrrol-2-yl)-7-[2-(pyridin-2-yl)ethyl]-benzoxazole This is prepared from 2-amino-4-chloro-6-[2-(pyridin-2-yl)ethyl]phenol and 1-methyl-2-pyrrole-carbonyl chloride (prepared from the corresponding carboxylic acid with oxalyl chloride) using method A with ethyl acetate as solvent to give the intermediate amide (30%). This is cyclised using methanesulphonic acid in toluene at reflux under standard conditions to give the title compound (8%), as a white crystalline solid, m.p. 100–101° C. TLC (SiO$_2$, EtOAc:hexanes 1:1, Rf=0.65). Mass spectrum CI (methane) m/z=337 [M+H]$^+$.

EXAMPLE 16
Preparation of 5-chloro-7-[2-(pyridin-2-yl)ethyl]-2-(quinolin-8-yl)-benzoxazole This is prepared by reaction of 2-amino-4-chloro-6-[2-(pyridin-2-yl)ethyl]phenol with 8-quinoline carbonyl chloride (prepared from the corresponding carboxylic acid using oxalyl chloride) using method A to give the intermediate amide (99%). This is cyclised with methanesulphonic acid in toluene at reflux under standard conditions to give the title compound (20%), m.p. 110–111° C. TLC (SiO$_2$, EtOAc:hexanes 1:1, Rf=0.18). Mass spectrum CI (methane) m/z=386 [M+H]$^+$.

EXAMPLE 17
Preparation of 5-chloro-2-(5-fluoroindol-2-yl)-7-[2-(pyridin-2-yl)ethyl]-benzoxazole This is prepared by reaction of 2-amino-4-chloro-6-[2-(pyridin-2-yl)ethyl]phenol with 5-fluoroindole-2-carbonyl chloride (prepared by reaction of the corresponding carboxylic acid with oxalyl chloride ) using method A, with 1,4-dioxan as solvent to give the intermediate amide (99%). This is cyclised using methanesulphonic acid in toluene at reflux under standard conditions to give the title compound (5%), as a pale yellow solid m.p. 194–196° C. TLC (hexanes:ethyl acetate 2:1, Rf=0.41). Mass spectrum CI (methane) m/z=392 [M+H]$^+$.

EXAMPLE 18
Preparation of 5-chloro-2-(imidazol-5-yl)-7-[2-(pyridin-2-yl)ethyl]-benzoxazole This is prepared from 2-amino-4-chloro-6-[2-(pyridin-2-yl)ethyl]-phenol and 4-imidazolecarbonyl chloride hydrochloride (prepared from the corresponding carboxylic acid with oxalyl chloride) using method A with 1,4-dioxan as solvent to give the intermediate amide (53%). This is cyclised using methanesulphonic acid in toluene at reflux using standard conditions to give the title compound (7%), as a pale yellow solid, m.p. 202–209° C. TLC (SiO$_2$, chloroform:methanol 9:1, Rf=0.62). Mass spectrum CI(methane) m/z=325 [M+H]$^+$.

EXAMPLE 19
Preparation of 5-chloro-2-(pyrazol-4-yl)-7-[2-(pyridin-2-yl) ethyl]-benzoxazole This is prepared by reaction of 2-amino-4-chloro-6-[2-(pyridin-2-yl)ethyl]phenol with 4-pyrazolecarbonyl chloride (prepared by reaction of the corresponding carboxylic acid with oxalyl chloride), using method A with 1,4 -dioxan as solvent to give the intermediate amide (16%). This is cyclised using methanesulphonic acid in toluene at reflux under standard conditions to give the title compound (16%), as a white solid, m.p. 204–208° C. TLC (SiO$_2$, chloroform:methanol 4:1, Rf=0.50). Mass spectrum CI (methane) m/z= 325 [M+H]$^+$.

EXAMPLE 20
Preparation of 5-chloro-2-(furan-3-yl)-7-[2-(pyridin-2-yl) ethyl]-benzoxazole This is prepared by reaction of 2-amino-4-chloro-6-[2-(pyridin-2-yl)ethyl] phenol with 3-furoyl chloride using method A with 1,4-dioxan as solvent to give the intermediate amide (87%). This is cyclised using methanesulphonic acid in toluene at reflux under standard conditions to give the title compound as an ivory solid, m.p. 114–1 15° C. TLC (SiO$_2$, EtOAc:hexanes 1:1, Rf=0.53). Mass spectrum CI (methane) m/z=325 [M+H]$^+$.

EXAMPLE 21
Preparation of 5-chloro-2-(2,4-dimethyl-furan-3-yl)-7-[2-(pyridin-2-yl)ethyl]-benzoxazole This is prepared by reaction of 2-amino-4-chloro-6-[2-(pyridin-2-yl)ethyl]phenol with 2,4-dimethyl-3-furoyl chloride (prepared in two steps from ethyl-2,4-dimethyl-3-furoate by hydrolysis followed by reaction of the carboxylic acid with oxalyl chloride) using method A with 1,4-dioxan as solvent to give intermediate amide (40%). This is cyclised with methanesulphonic acid in toluene at reflux under standard conditions to give the title compound (29%), as a pale yellow solid, m.p. 73–76° C. TLC (SiO$_2$, hexanes:EtOAc 2:1, Rf=0.53). Mass spectrum CI (methane) m/z=353 [M+H]$^+$.

EXAMPLE 22
Preparation of 5-chloro-7-[2-(pyridin-2-yl)ethyl]-2-(tetrahydrofuran-3-yl)-benzoxazole This is prepared by reaction of 2-amino-4-chloro-6-[2-(pyridin-2-yl)ethyl]phenol with tetrahydro-3-furoyl chloride (prepared by reaction of the corresponding carboxylic acid by reaction with oxalyl chloride) using method A, with 1,4-dioxan as solvent to give the intermediate amide (100%). This is cyclised using methanesulphonic acid in refluxing toluene under standard conditions to give the title compound as a pale yellow oil. TLC (SiO$_2$, chloroform:methanol 95:5, Rf=0.45). Mass spectrum CI (methane) m/z=329 [M+H]$^+$.

Type IV Phosphodiesterase Enzyme Isolation Protocol

The type IV PDE is isolated from bovine tracheal smooth muscle using a procedure similar to that previously described by Silver, P. J. et al., Eur. J. Pharmacol. 85,150, 1988. Briefly, smooth muscle from bovine trachea is minced and homogenised using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000× g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialysed and concentrated to 14% of the original volume. The concentrated fractions are diluted to 50% with ethylene glycol and stored at –20° C. PDE IV can typically be stored for up to four weeks.

Measuring Type IV PDE Activity

Enzyme activity is assessed by measuring the hydrolysis of [$^3$H]-cyclic AMP, as described by Thomson, W. J. et al., Adv. Cyclic Nucleotide Res., 69, 10, 1979. The cyclic AMP concentration used in this assay is 0.2 $\mu$M, which approximates the K$_m$ value. Protein concentration is adjusted to ensure that no more than 15% of the available substrate is hydrolysed during the incubation period. All test compounds are dissolved in dimethyl sulphoxide (final concentration of 2.5%). This concentration of dimethyl sulphoxide inhibits enzyme activity by approximately 10%.

Following the above procedure, the PDE IV, enzyme inhibition (as an IC$_{50}$/$\mu$M) for the compounds of Examples 1–23, and rolipram are tested and compared. The results are shown in table 1.

TABLE 1

| Compound | PDE IV IC$_{50}$/$\mu$M |
| --- | --- |
| 5-chloro-2-(furan-2-yl)-7-[2-(pyridin-2-yl)ethyl]-benzoxazole | 0.19 |
| 5-chloro-2-(pyridin-4-yl)-7-[2-(pyridin-2-yl)-ethyl]-benzoxazole | 1.25 |
| 5-chloro-7-[2-(pyridin-2-yl)ethyl]-2-(thien-2-yl)-benzoxazole | 0.73 |

TABLE 1-continued

| Compound | PDE IV IC$_{50}$/$\mu$M |
|---|---|
| 5-chloro-7-[2-(pyridin-2-yl)ethyl]-2-(thien-3-yl)-benzoxazole | 0.55 |
| 2-(benzo[b]thien-2-yl)-5-chloro-7-[2-(pyridin-2-yl)ethyl]-benzoxazole | 0.46 |
| 2-(isoquinolin-1-yl)-5-chloro-7-[2-(pyridin-2-yl)ethyl]-benzoxazole | 4.35 |
| 5-chloro-2-[4-methyl-(1,2,3-thiadiazol-5-yl)]-7-[2-(pyridin-2-yl)ethyl]-benzoxazole | 5.93 |
| 5-chloro-7-[2-(pyridin-2-yl)ethyl]-2-(quinoxalin-2-yl)-benzoxazole | 96.26 |
| 5-chloro-7-[2-(pyridin-2-yl)ethyl]-2-(quinolin-3-yl)-benzoxazole | 3.88 |
| 5-chloro-2-(pyrazin-2-yl)-7-[2-(pyridin-2-yl)ethyl]-benzoxazole | 1.53 |
| 5-chloro-2-(isoxazol-5-yl)-7-[2-(pyridin-2-yl)ethyl]-benzoxazole | 2.52 |
| 5-chloro-2-(3-methyl-pyrazol-5-yl)-7-[2-(pyridin-2-yl)ethyl]-benzoxazole | 0.95 |
| 2-(benzotriazol-5-yl)-5-chloro-7-[2-(pyridin-2-yl)ethyl]-benzoxazole | 0.23 |
| 5-chloro-2-(5-methoxyindol-2-yl)-7-[2-(pyridin-2-yl)ethyl]-benzoxazole | 0.16 |
| 5-chloro-2-(1-methylpyrrol-2-yl)-7-[2-(pyridin-2-yl)ethyl]-benzoxazole | 3.65 |
| 5-chloro-7-[2-(pyridin-2-yl)ethyl]-2-(quinolin-8-yl)-benzoxazole | 1.23 |
| 5-chloro-2-(5-fluoroindol-2-yl)-7-[2-(pyridin-2-yl)ethyl]-benzoxazole | 1.64 |
| 5-chloro-2-(imidazol-5-yl)-7-[2-(pyridin-2-yl)ethyl]-benzoxazole | 4.54 |
| 5-chloro-2-(pyrazol-4-yl)-7-[2-(pyridin-2-yl)ethyl]-benzoxazole | 4.03 |
| 5-chloro-2-(furan-3-yl)-7-[2-(pyridin-2-yl)ethyl]-benzoxazole | 0.84 |
| 5-chloro-2-(2,4-dimethyl-furan-3-yl)-7-[2-(pyridin-2-yl)ethyl]-benzoxazole | 0.49 |
| 5-chloro-7-[2-(pyridin-2-yl)ethyl]-2-(tetrahydrofuran-3-yl)-benzoxazole | 5.50 |
| Rolipram | 3.7 |

While the invention has been illustrated with respect to the production and use of particular compounds, it is apparent that variations and modifications of the invention can be made without departing from the spirit or scope of the invention.

What is claimed is:

1. A compound having the formula (I):

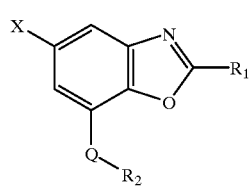

(I)

wherein:

X is halogen;

Q is —CH$_2$—CH$_2$—, —CH$_2$—, or a bond;

R$_1$ is pyridyl unsubstituted or substituted with C$_{1-8}$alkyl, C$_{3-7}$cycloalkyl, C$_{1-8}$alkoxy, C$_{3-7}$cycloalkoxy, hydroxy or halogen; or is a 3–5 or 7 membered monocyclic ring structure consisting of at least one carbon atom and one or more heteroatoms selected from the group consisting of nitrogen, sulfur and oxygen, wherein the monocyclic ring structure may be unsubstituted or substituted with C$_{1-8}$alkyl, C$_{3-7}$cycloalkyl, C$_{1-8}$alkoxy, C$_{3-7}$cycloalkoxy, hydroxy or halogen; or is a bicyclic aryl ring structure consisting of a phenyl ring fused to a 3–7 membered monocyclic ring structure, said monocyclic ring structure consisting of at least one carbon atom and one or more heteroatoms selected from the group consisting of nitrogen, sulfur and oxygen, wherein said monocyclic ring is unsaturated, partially unsaturated or saturated, and is optionally substituted with C$_{1-8}$alkyl, C$_{3-7}$cycloalkyl, C$_{1-8}$alkoxy, C$_{3-7}$cycloalkoxy, hydroxy or halogen;

R$_2$ is pyridyl unsubstituted or substituted with C$_{1-8}$alkyl, C$_{3-7}$cycloalkyl, C$_{1-8}$alkoxy, C$_{3-7}$cycloalkoxy, hydroxy or halogen; or a 3–7 membered monocyclic ring structure consisting of at least one carbon atom and one or more heteroatoms selected from the group consisting of nitrogen, sulfur and oxygen, wherein said monocyclic ring is optionally substituted with C$_{1-8}$alkyl, C$_{3-7}$cycloalkyl, C$_{1-8}$alkoxy, C$_{3-7}$cycloalkoxy, hydroxy or halogen;

provided that at least one of R$_1$ and R$_2$ is pyridyl.

2. A compound of claim 1, selected from the group consisting of:

5-chloro-2-(furan-2-yl)-7-[2-(pyridin-2-yl)ethyl]-benzoxazole;

5-chloro-2-(pyridin-4-yl)-7-[2-(pyridin-2-yl)ethyl]-benzoxazole;

5-chloro-7-[2-(pyridin-2-yl)ethyl]-2-(thien-2-yl)-benzoxazole;

5-chloro-7-[2-(pyridin-2-yl)ethyl]-2-(thien-3-yl)-benzoxazole;

2-(benzo[b]thien-2-yl)-5-chloro-7-[2-(pyridin-2-yl)ethyl]-benzoxazole;

2-(isoquinolin-1-yl)-5-chloro-7-[2-(pyridin-2-yl)ethyl]-benzoxazole;

5-chloro-2-[4-methyl-(1,2,3-thiadiazol-5-yl)]-7-[2-(pyridin-2-yl)ethyl]-benzoxazole;

5-chloro-7-[2-(pyridin-2-yl)ethyl]-2-(quinoxalin-2-yl)-benzoxazole;

5-chloro-2-(isoxazol-5-yl)-7-[2-(pyridin-2-yl)ethyl]-benzoxazole;

5-chloro-2-(3-methyl-pyrazol-5-yl)-7-[2-(pyridin-2-yl)ethyl]-benzoxazole;

2-(benzotriazol-5-yl)-5-chloro-7-[2-(pyridin-2-yl)ethyl]-benzoxazole;

5-chloro-2-(5-methoxyindol-2-yl)-7-[2-(pyridin-2-yl)ethyl]-benzoxazole;

5-chloro-2-(1-methylpyrrol-2-yl)-7-[2-(pyridin-2-yl)ethyl]-benzoxazole;

5-chloro-7-[2-(pyridin-2-yl)ethyl]-2-(quinolin-8-yl)-benzoxazole;

5-chloro-2-(5-fluoroindol-2-yl)-7-[2-(pyridin-2-yl)ethyl]-benzoxazole;

5-chloro-2-(imidazol-5-yl)-7-[2-(pyridin-2-yl)ethyl]-benzoxazole;

5-chloro-2-(pyrazol-4-yl)-7-[2-(pyridin-2-yl)ethyl]-benzoxazole;

5-chloro-2-(furan-3-yl)-7-[2-(pyridin-2-yl)ethyl]-benzoxazole;

5-chloro-2-(2,4-dimethyl-furan-3-yl)-7-[2-(pyridin-2-yl)ethyl]-benzoxazole; and 5-chloro-7-[2-(pyridin-2-yl)ethyl]-2-(tetrahydrofuran-3-yl)-benzoxazole.

3. A pharmaceutical composition comprising an effective amount of a compound of claim 1.

4. The compound of claim 1 wherein $R_2$ is pyridyl.

5. The compound of claim 4 wherein Q is —$CH_2$—$CH_2$.

6. The compound of claim 5 wherein X is chloride.

7. The compound of claim 1 wherein $R_1$ is selected from the group consisting of furanyl, pyridyl, thienyl, benzothienyl, isoquinolinyl, methylthiadiazolyl, quinoxalinyl, pyrazinyl, isoxazolyl, methylpyrazolyl, benzotriazolyl, methoxyindolyl, methylpyrrolyl, quinolinyl, fluoroindolyl, imidazolyl, pyrazolyl, dimethylfuranyl and tetrahydrofuranyl.

8. The compound of claim 1 wherein $R_1$ is a 5 membered heteroaryl ring.

9. The compound of claim 8 wherein $R_2$ is pyridyl.

10. The compound of claim 1, wherein said monocyclic ring structure is aromatic.

11. The compound of claim 1, wherein $R_1$ is a 5 membered monocyclic ring.

* * * * *